(12) United States Patent
Yumikake et al.

(10) Patent No.: US 8,098,278 B2
(45) Date of Patent: Jan. 17, 2012

(54) OPTICAL IMAGE MEASUREMENT DEVICE

(75) Inventors: Kazuhiko Yumikake, Tokyo (JP);
Hiroaki Okada, Tokyo (JP); Tsutomu Kikawa, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 261 days.

(21) Appl. No.: 12/451,621

(22) PCT Filed: May 15, 2008

(86) PCT No.: PCT/JP2008/001213
§ 371 (c)(1),
(2), (4) Date: Nov. 20, 2009

(87) PCT Pub. No.: WO2008/142854
PCT Pub. Date: Nov. 27, 2008

(65) Prior Publication Data
US 2010/0118132 A1    May 13, 2010

(30) Foreign Application Priority Data

May 24, 2007    (JP) ................... 2007-137771

(51) Int. Cl.
*H04N 7/18* (2006.01)
*H04N 9/47* (2006.01)
*A61B 3/14* (2006.01)

(52) U.S. Cl. .......................... 348/78; 351/206
(58) Field of Classification Search ............... 348/78; 351/206
See application file for complete search history.

(56) References Cited

U.S. PATENT DOCUMENTS
5,847,827 A * 12/1998 Fercher .............. 356/493

2005/0140984 A1    6/2005  Hitzenberger
2006/0187462 A1    8/2006  Srinivasan et al.
2007/0285619 A1*  12/2007  Aoki et al. ........... 351/206

FOREIGN PATENT DOCUMENTS

| EP | 1 842 483 A1 | 10/2007 |
|---|---|---|
| JP | 08-000565 A | 1/1996 |
| JP | 11-325849 A | 11/1999 |
| JP | 2002-139421 A | 5/2002 |
| JP | 2003-000543 A | 1/2003 |
| JP | 2006-061328 A | 3/2006 |
| JP | 2007-117714 A | 5/2007 |
| WO | WO-2006-105903 | 10/2006 |

OTHER PUBLICATIONS

International Search Report mailed Jul. 15, 2008, issued on PCT/JP2008/001213.
Supplementary European Search Report for European Patent Application No. 08 75 1731 issued Feb. 2, 2011.

* cited by examiner

*Primary Examiner* — David Czekaj
*Assistant Examiner* — Anner Holder
(74) *Attorney, Agent, or Firm* — Edwards Wildman Palmer LLP

(57) ABSTRACT

A fundus oculi observation device 1 splits a low-coherence light L0 into a signal light LS and a reference light LR, generates an interference light LC from the signal light LS propagated through an eye E and the reference light LR propagated through a reference mirror 174 to detect the interference light LC and, based on the result of the detection, forms a tomographic image of a fundus oculi Ef. The device 1 includes a scan unit 141 configured to scan with the signal light LS, and an LCD and optical system that present a fixation target. The device 1 acquires an image of the fundus oculi Ef in a state that scan a fixation target is presented while scanning with the signal light LS, and based on the image, determines whether fixation is proper or not.

12 Claims, 10 Drawing Sheets

OPTICAL IMAGE MEASUREMENT DEVICE

TECHNICAL FIELD

The present invention relates to an optical image measurement device that scans an eye with a light beam and forms an image by using the reflected light.

BACKGROUND ART

In recent years, attention has been focused on an optical image measurement technique of forming an image showing the surface morphology or internal morphology of a measurement object by using a light beam emitted from a laser light source or the like. Because this optical image measurement technique does not have invasiveness to human bodies unlike an X-ray CT device, it is expected to employ this technique particularly in the medical field.

Patent Document 1 discloses an optical image measurement device configured in a manner that: a measuring arm scans an object by using a rotary deflection mirror (Galvano mirror); a reference mirror is disposed to a reference arm; at the outlet thereof, such an interferometer is used that the intensity of a light caused by interference of light fluxes from the measuring arm and the reference arm is analyzed by a spectrometer; and the reference arm is provided with a device gradually changing the light flux phase of the reference light in non-continuous values.

The optical image measurement device disclosed in Patent Document 1 uses a method of so-called "Fourier Domain OCT (Optical Coherence Tomography)." That is to say, the morphology of a measurement object in the depth direction (z-direction) is imaged by applying a beam of a low-coherence light to the measurement object, obtaining the spectrum intensity distribution of the reflected light, and subjecting the obtained distribution to Fourier transform.

Furthermore, the optical image measurement device described in Patent Document 1 is provided with a Galvano mirror scanning with a light beam (a signal light), thereby being capable of forming an image of a desired measurement region of a measurement object. Because this optical image measurement device scans with the light beam only in one direction (x-direction) orthogonal to the z-direction, a formed image is a 2-dimensional tomographic image in the depth direction (z-direction) along the scanning direction of the light beam (the x-direction).

Further, Patent Document 2 discloses a technique of scanning with a signal light in both the horizontal and vertical directions to thereby form a plurality of 2-dimensional tomographic images in the horizontal direction and, based on the plurality of tomographic images, acquiring and imaging 3-dimensional tomographic information of a measurement range. A method for 3-dimensional imaging is, for example, a method of arranging and displaying a plurality of tomographic images in the vertical direction (referred to as stack data or the like), and a method of forming a 3-dimensional image by subjecting a plurality of tomographic images to a rendering process.

Further, Patent Document 3 discloses a configuration of using such an optical image measurement device in the ophthalmic field.

[Patent Document 1] Japanese Unexamined Patent Application Publication No. 11-325849
[Patent Document 2] Japanese Unexamined Patent Application Publication No. 2002-139421
[Patent Document 3] Japanese Unexamined Patent Application Publication No. 2003-543

DISCLOSURE OF THE INVENTION

Problem that the Invention is to Solve

When an optical image measurement device is used in the ophthalmic field, the following problem may arise. Specifically in an optical image measurement device that scans an eye with a light beam, since a low-coherence light having a center wavelength of near-infrared region is generally used and the low-coherence light includes visible-light components, there is a case that a subject follows the trajectory of the scan with his/her eye and an accurate image cannot be acquired.

For example, in the case of scan with a signal light as in Patent Document 2, a subject visually recognizes a linear image that moves in the vertical direction, and the subject's eye often moves in the vertical direction.

Although it is necessary to fix an eye in order to prevent the above problem, it is difficult to fix the eye with conventional devices.

Further, according to conventional devices, since an examiner cannot know whether an eye is properly fixed, a measurement may be executed in the improperly fixed state. This causes a problem such that a low-accuracy image is acquired and a re-measurement is required.

The present invention was made to solve these problems, and an object of the present invention is to provide an optical image measurement device that is capable of preventing an eye from following the trajectory of a scan with a signal light.

Means for Solving the Above Problem

In order to achieve the above object, in a first aspect of the present invention, an optical image measurement device that splits a low-coherence light into a signal light and a reference light, superimposes the signal light propagated through an eye and the reference light propagated through a reference object to generate an interference light, detects the interference light, and forms a tomographic image of the eye based on a detection result, comprises: a scanner configured to scan the eye with the signal light; a presenting part configured to present a fixation target for fixing the eye; a controller configured to control the presenting part to present the fixation target in the eye, and control the scanner to scan the eye with the signal light; and a determining part configured to acquire an image of the eye in which the fixation target is presented and which is scanned with the signal light, and determine whether a fixation state of the eye is proper, based on the image.

Further, in a second aspect of the present invention, the optical image measurement device according to the first aspect is characterized in that the determining part is configured to analyze the image to specify an image position of a characteristic site of the eye within the image, and determine whether the fixation state is proper, based on the image position.

Further, in a third aspect of the present invention, the optical image measurement device according to the second aspect is characterized in that the determining part is configured to obtain a displacement of the image position with respect to a predetermined position in a frame of the image, and determine whether the fixation state is proper, based on the displacement.

Further, in a fourth aspect of the present invention, the optical image measurement device according to the third aspect is characterized in that the determining part is configured to determine the fixation state is proper when a size of the displacement is equal to or less than a predetermined threshold, and to determine the fixation state is improper when the size of the displacement is more than the predetermined threshold.

Further, in a fifth aspect of the present invention, the optical image measurement device according to the third aspect further comprises a corrector configured to correct a position of the tomographic image based on the displacement at least when it is determined that the fixation state is improper.

Further, in a sixth aspect of the present invention, the optical image measurement device according to the second aspect is characterized in that the determining part is configured to determine whether the image position is included in a predetermined region within a frame of the acquired image, and to determine the fixation state is proper when it is determined that the image position is included and determine the fixation state is improper when it is determined that the image position is not included.

Further, in a seventh aspect of the present invention, the optical image measurement device according to the first aspect is characterized in that the determining part includes an imaging part configured to capture an image of a fundus oculi surface of the eye to acquire a two-dimensional image as the image, and is configured to determine whether the fixation state is proper, based on the two-dimensional image.

Further, in an eighth aspect of the present invention, the optical image measurement device according to the first aspect is characterized in that the determining part includes an image forming part configured to form the tomographic image as the image, and is configured to determine whether the fixation state is proper, based on the tomographic image.

Further, in a ninth aspect of the present invention, the optical image measurement device according to the first aspect is characterized in that the determining part is configured to acquire a motion image of a fundus oculi of the eye, and is configured to determine whether the fixation state is proper for each frame of the motion image.

Further, in a tenth aspect of the present invention, the optical image measurement device according to the first aspect further comprises an output part configured to output a determination result of the fixation state by the determining part.

Further, in an eleventh aspect of the present invention, the optical image measurement device according to the first aspect is characterized in that: the presenting part is configured to be capable of selectively presenting a plurality of fixation targets of different fixation positions; and the determining part is configured to determine whether the fixation state is proper in response to a fixation position of a presented fixation target.

Further, in a twelfth aspect of the present invention, an optical image measurement device that splits a low-coherence light into a signal light and a reference light, superimposes the signal light propagated through an eye and the reference light propagated through a reference object to generate an interference light, detects the interference light, and forms a tomographic image of the eye based on a detection result, comprises: a scanner configured to scan the eye with the signal light; a presenting part configured to present a fixation target for fixing the eye; and a controller configured to, before detection of the interference light for forming the tomographic image of the eye, control the presenting part to present the fixation target in the eye, and control the scanner to scan the eye with the signal light.

Effect of the Invention

According to the present invention, it is possible to properly fix an eye by acquiring an image of the eye in a state that the eye is scanned with a signal light while a fixation target is presented in the eye and, based on the image, determine whether a fixation state of the eye is proper. This can prevent the eye from following the trajectory of the scan.

Further, according to the present invention, by scanning an eye with a signal light while presenting a fixation target in the eye before detecting an interference light for forming a tomographic image of the eye, a subject can practice fixation in the state of visually recognizing the trajectory of the scan with the signal light. This can prevent the eye from following the trajectory of the scan with the signal light.

BRIEF DESCRIPTION OF THE DRAWINGS

FIG. 7A shows an example of the scanning pattern of the signal light when the fundus oculi is seen from the incident side of the signal light into an eye. FIG. 7B shows an example of an arrangement pattern of scanning points on each scanning line.

Figure 1:
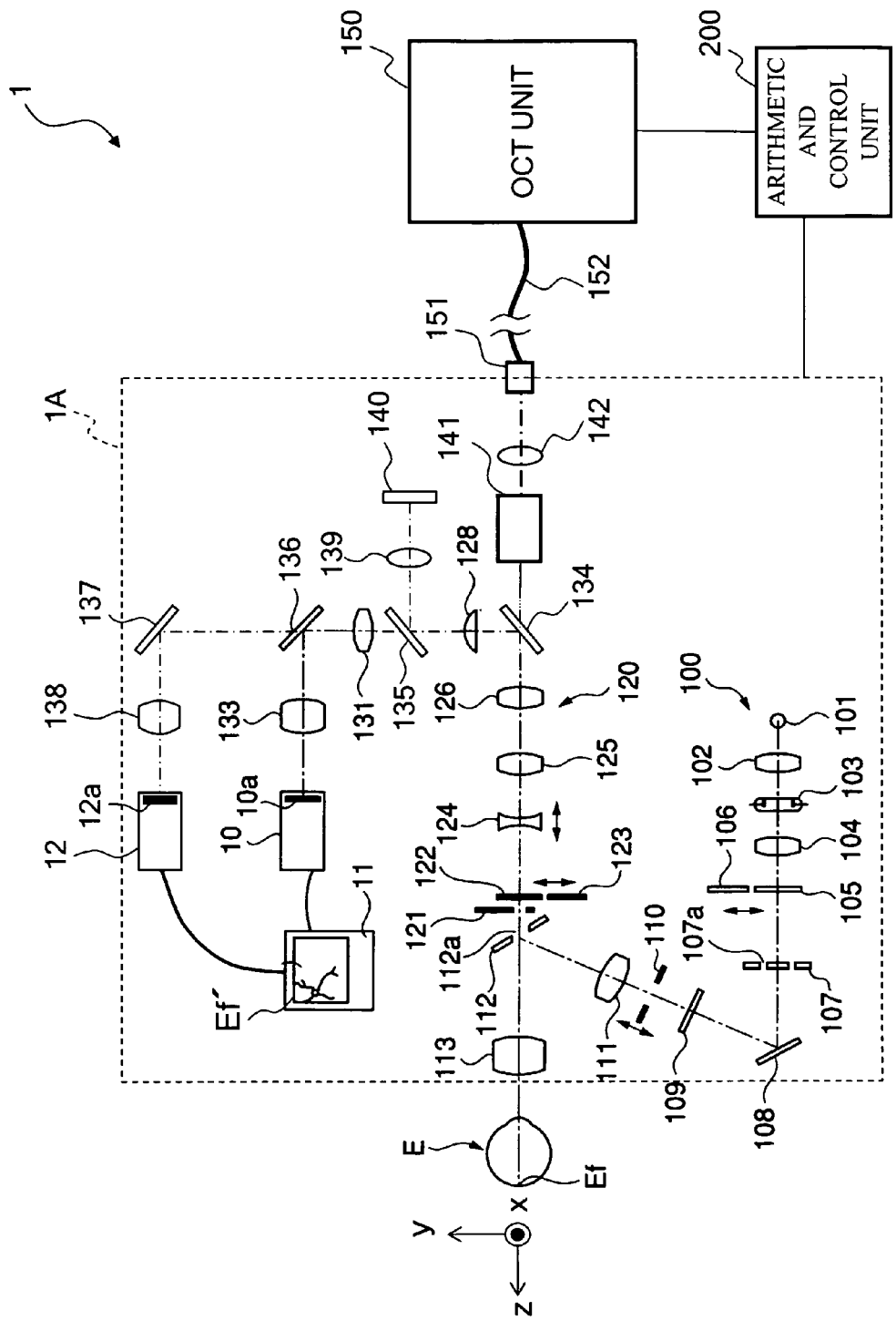
FIG. 1 is a schematic configuration diagram showing an example of the entire configuration in an embodiment of a fundus oculi observation device functioning as the optical image measurement device according to the present invention.

DESCRIPTION OF REFERENCE NUMERALS AND SYMBOLS 1 fundus oculi observation device (optical image measurement device)
1A retinal camera unit
140 LCD
141 scan unit
150 OCT unit
160 low-coherence light source
162 optical coupler
174 reference mirror
180 spectrometer
184 CCD
200 arithmetic and control unit
210 controller
211 main controller
212 storage
220 image forming part
230 image processor
231 fixation-state determining part
232 image position corrector
240 user interface
240A display
240B manipulation part
241, 242 mirror drive mechanisms
Ri(i=1–m) scanning line
E eye
Ef fundus oculi

BEST MODE FOR CARRYING OUT THE INVENTION

An example of an embodiment of an optical image measurement device according to the present invention will be described in detail with reference to the drawings.

The present invention is used in the ophthalmic field. The present invention is to certainly fix an eye by automatically determining whether a fixation state of the eye is proper. Moreover, the present invention is to practice fixation by previously presenting a situation that the subject visually recognizes at the time of acquiring an actual image, thereby securing fixation at the time of acquisition of an image.

[Device Configuration]

Figure 2:
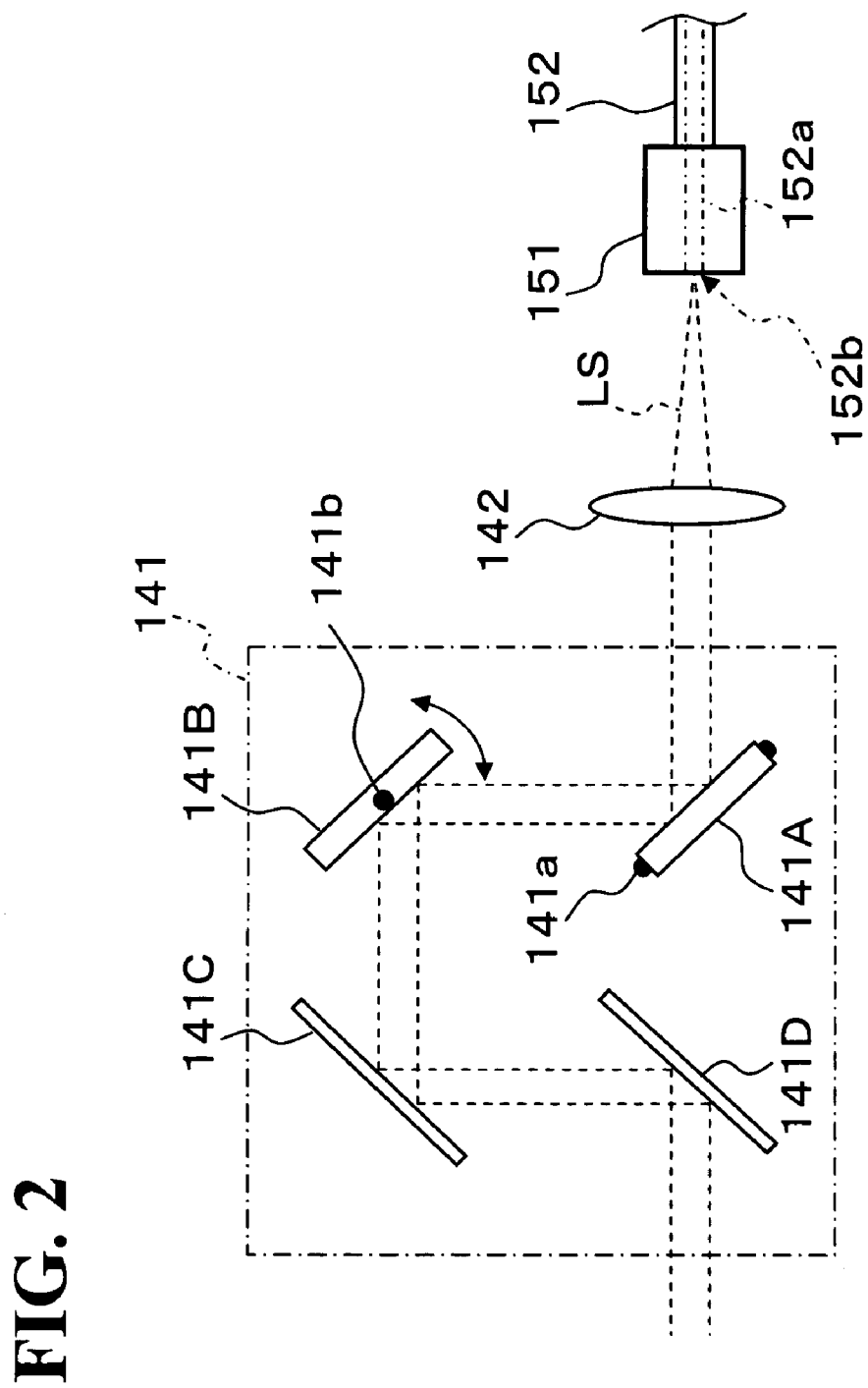
FIG. 2 is a schematic configuration diagram showing an example of the configuration of a scan unit installed in a retinal camera unit in the embodiment of the fundus oculi observation device functioning as the optical image measurement device according to the present invention.
Figure 3:
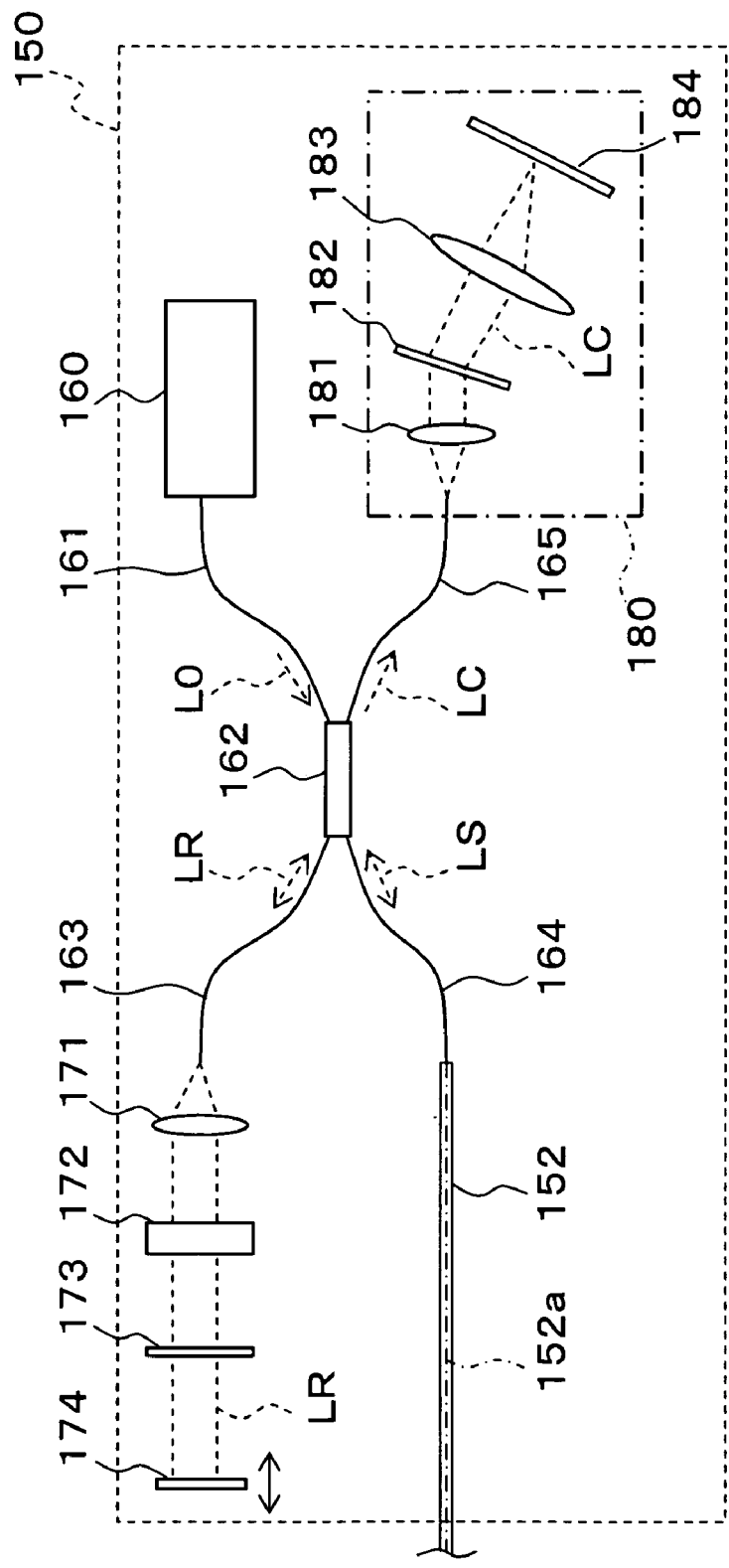
FIG. 3 is a schematic configuration diagram showing an example of the configuration of an OCT unit in the embodiment of the fundus oculi observation device functioning as the optical image measurement device according to the present invention.
Figure 4:
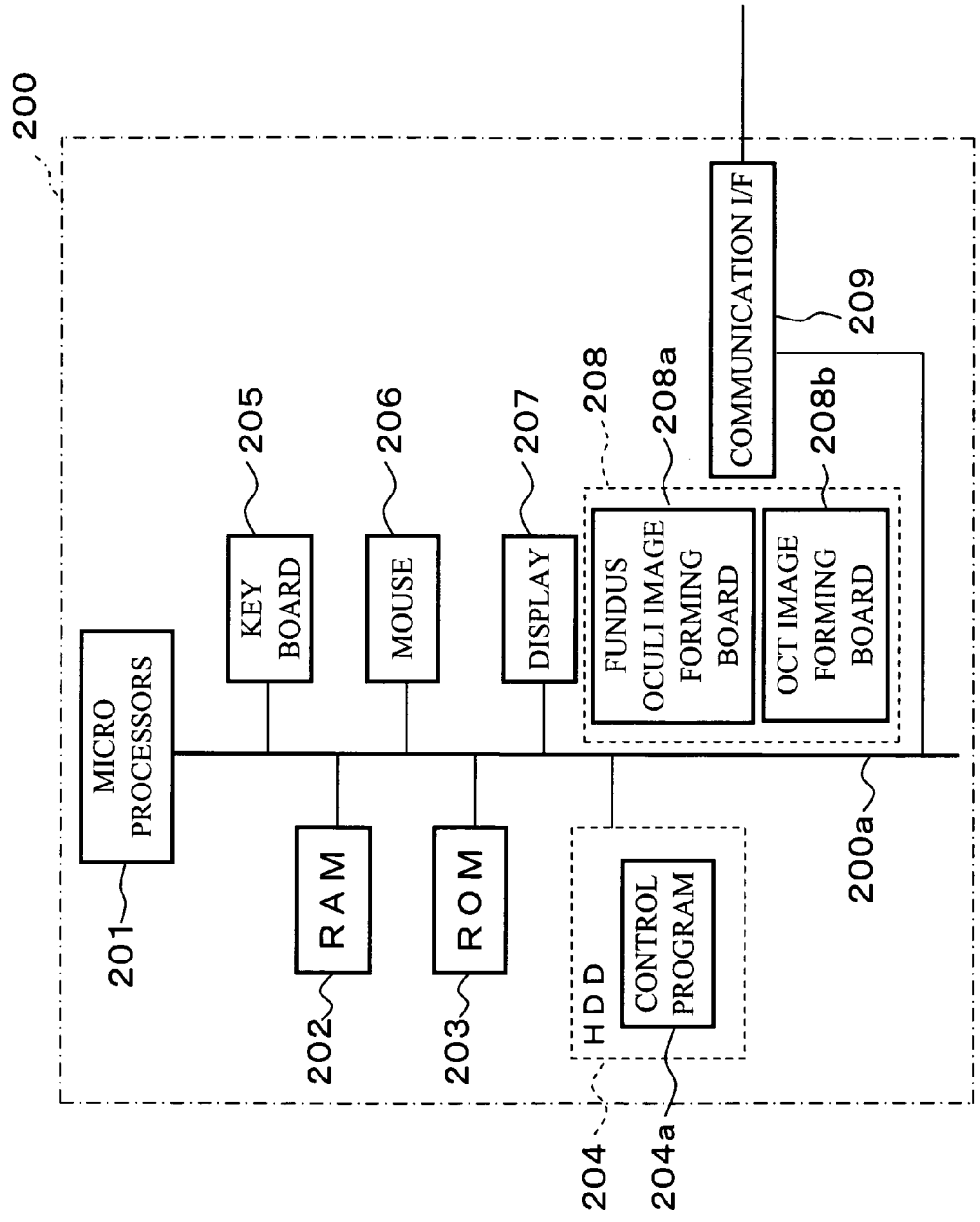
FIG. 4 is a schematic block diagram showing an example of the hardware configuration of an arithmetic and control unit in the embodiment of the fundus oculi observation device functioning as the optical image measurement device according to the present invention.
Figure 5:
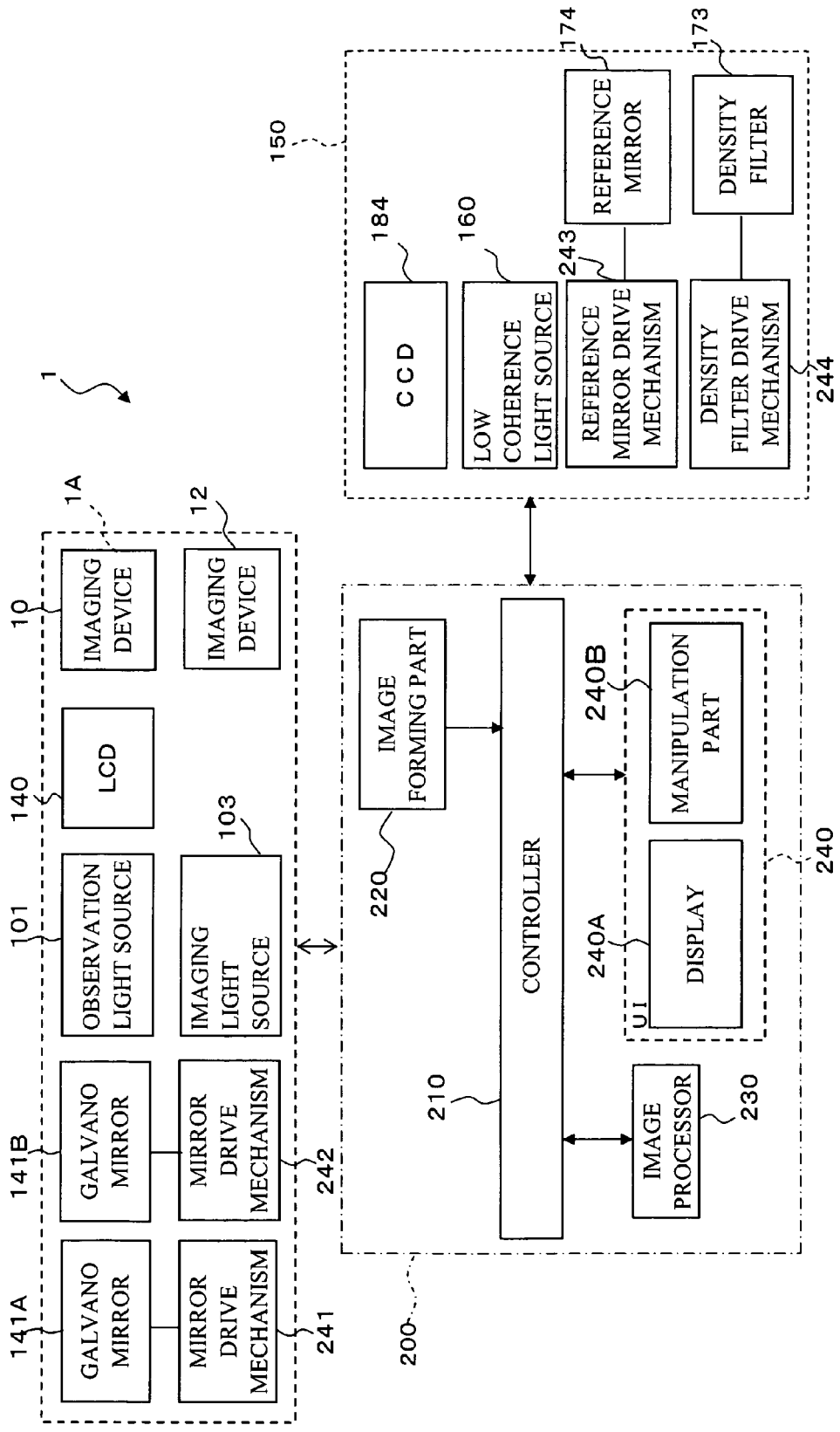
FIG. 5 is a schematic block diagram showing an example of the configuration of a control system in the embodiment of the fundus oculi observation device functioning as the optical image measurement device according to the present invention.
Figure 6:
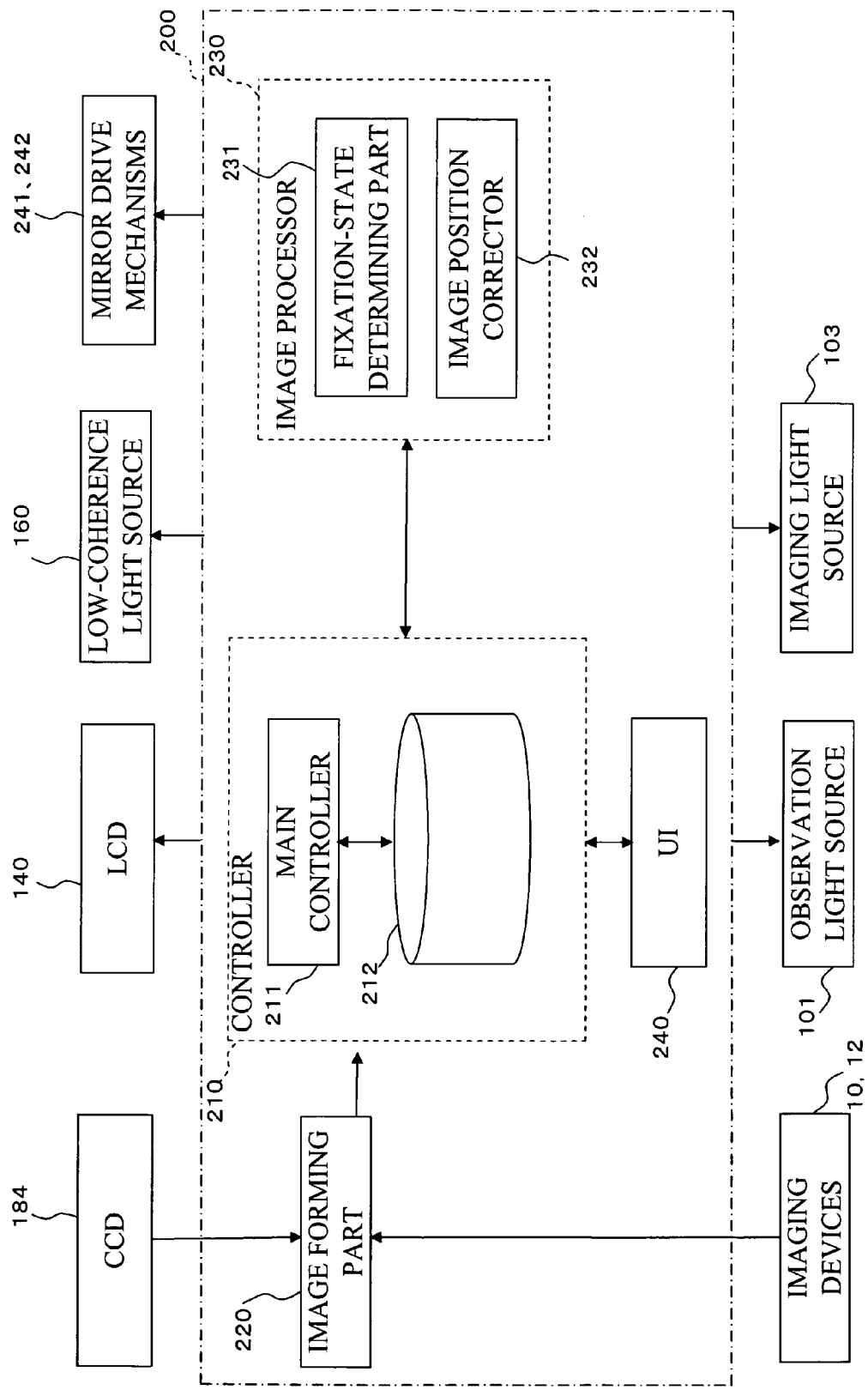
FIG. 6 is a schematic block diagram showing an example of the configuration of a control system in the embodiment of the fundus oculi observation device functioning as the optical image measurement device according to the present invention.

First, with reference to FIGS. 1 to 6, the configuration in an embodiment of the optical image measurement device according to the present invention will be described. FIG. 1 shows an example of the entire configuration of a fundus oculi observation device 1 having a function as the optical image measurement device according to the present invention. FIG. 2 shows an example of the configuration of a scan unit 141 in a retinal camera unit 1A. FIG. 3 shows an example of the configuration of an OCT unit 150. FIG. 4 shows an example of the hardware configuration of an arithmetic and control unit 200. FIGS. 5 and 6 show an example of the configuration of a control system of the fundus oculi observation device 1.

[Entire Configuration]

The fundus oculi observation device 1 includes the retinal camera unit 1A, the OCT unit 150, and the arithmetic and control unit 200 as shown in FIG. 1. The retinal camera unit 1A has almost the same optical system as a conventional retinal camera that captures a 2-dimensional image of the fundus oculi surface. The OCT unit 150 houses an optical system that functions as the optical image measurement device. The arithmetic and control unit 200 is provided with a computer that executes various kinds of arithmetic processes, control processes and so on.

To the OCT unit 150, one end of a connection line 152 is attached. A connector part 151 connecting the connection line 152 to the retinal camera unit 1A is attached to the other end of the connection line 152. A conductive optical fiber runs through inside the connection line 152. Thus, the OCT unit 150 and the retinal camera unit 1A are optically connected via the connection line 152.

[Configuration of Retinal Camera Unit]

The retinal camera unit 1A is used to capture a two-dimensional image of the fundus oculi surface of an eye based on optically acquired data (data detected by imaging devices 10 and 12). The 2-dimensional image of the fundus oculi surface is, for example, a color image or monochrome image of the fundus oculi surface, and a fluorescence image (a fluorescein fluorescence image, an indocyanine green fluorescence image, or the like). Moreover, the two-dimensional image may be either a still image or a motion image. The retinal camera unit 1A is an example of the "imaging part" of the present invention.

Like a conventional retinal camera, the retinal camera unit 1A is provided with an illumination optical system 100 that illuminates a fundus oculi Ef, and an imaging optical system 120 that guides the fundus oculi reflection light of the illumination light to the imaging device 10.

The imaging device 10 in the imaging optical system 120 detects an illumination light having a wavelength of near-infrared region, the details of which will be described later. The imaging optical system 120 is also provided with the imaging device 12 that detects an illumination light having a wavelength of visible region. The imaging optical system 120 guides a signal light coming from the OCT unit 150 to the fundus oculi Ef and guides the signal light propagated through the fundus oculi Ef to the OCT unit 150.

The illumination optical system 100 includes an observation light source 101, a condenser lens 102, an imaging light source 103, a condenser lens 104, exciter filters 105 and 106, a ring transparent plate 107, a mirror 108, an LCD (Liquid Crystal Display) 109, an illumination diaphragm 110, a relay lens 111, an aperture mirror 112, and an objective lens 113.

The observation light source 101 outputs an illumination light having a wavelength of visible region included in a range of about 400~700 nm, for example. On the other hand, the imaging light source 103 outputs an illumination light having a wavelength of near-infrared region included in a range of about 700~800 nm, for example. The near-infrared light outputted from the imaging light source 103 is set so as to have a shorter wavelength than the light used by the OCT unit 150 (described later).

The imaging optical system 120 includes the objective lens 113, the (aperture 112a of the) aperture mirror 112, an imaging diaphragm 121, barrier filters 122 and 123, a variable magnifying lens 124, a relay lens 125, an imaging lens 126, a dichroic mirror 134, a field lens 128, a half mirror 135, a relay lens 131, a dichroic mirror 136, an imaging lens 133, the imaging device 10 (an image pick-up element 10a), a reflection mirror 137, an imaging lens 138, the imaging device 12 (an image pick-up element 12a), a lens 139, and an LCD 140.

Furthermore, the imaging optical system 120 includes the dichroic mirror 134, the half mirror 135, the dichroic mirror 136, the reflection mirror 137, the imaging lens 138, the lens 139, and the LCD 140.

The dichroic mirror 134 is configured to reflect the fundus oculi reflection light (having a wavelength included in a range of about 400~800 nm) of the illumination light coming from the illumination optical system 100, and to transmit a signal light LS (having a wavelength included in a range of, for example, about 800~900 nm; described later) coming from the OCT unit 150.

The dichroic mirror 136 is configured to transmit the illumination light having a wavelength of visible region coming from the illumination optical system 100 (a visible light having a wavelength of about 400~700 nm outputted from the observation light source 101), and to reflect the illumination light having a wavelength of near-infrared region (a near-infrared light having a wavelength of about 700~800 nm outputted from the imaging light source 103).

The LCD 140 displays a fixation target (an internal fixation target) for fixing an eye E. A light from the LCD 140 is reflected by the half mirror 135 after being focused by the lens 139, and is reflected by the dichroic mirror 136 after propagated through the field lens 128. Furthermore, this light is propagated through the imaging lens 126, the relay lens 125, the variable magnifying lens 124, the (aperture 112a of the) aperture mirror 112, the objective lens 113, and so on, and enters the eye E. Consequently, an internal fixation target is projected onto the fundus oculi Ef of the eye E.

The LCD 140 and the optical elements for projecting an internal fixation target onto the fundus oculi Ef configure an example of the "presenting part" of the present invention. The presenting part is not limited to an LCD, and it is possible to use, for example, another display device, or a light source such as a plurality of two-dimensionally arranged LEDs (Light-Emitting Diodes).

It is possible to change the fixation position of the eye E by using the internal fixation target. The fixation position is, for example, a fixation position for acquiring an image in which the center of the fundus oculi is positioned in the center of the frame (a fixation position for the fundus oculi center), a fixation position for acquiring an image in which the macula (the fovea centralis) is positioned in the center of the frame (a fixation position for the macula), and a fixation position for acquiring an image in which the optic papilla is positioned in the center of the frame (a fixation position for the optic papilla). It is possible to apply any fixation position by operating a manipulation part 240B described later.

To change the fixation position, the LCD 140 displays the internal fixation target at a different position on the display surface. A main controller 211 described later controls the display position. Alternatively, it is possible to change the fixation position by controlling the optical system that projects the internal fixation target onto the fundus oculi Ef. In the case of using a presenting part that includes a plurality of light sources, it is possible to change the fixation position by changing a light source to turn on.

Designation of the fixation position is performed by, for example, an operator operating the manipulation part 240B. In a case that, for example, the fixation position is already known as in the case of a follow-up, it is possible to automatically designate the fixation position.

The image pick-up element 10a is an image pick-up element such as a CCD (Charge Coupled Device) or a CMOS (Complementary Metal Oxide Semiconductor) installed in the imaging device 10 such as a TV camera, and particularly detects a light having a wavelength of near-infrared region. In other words, the imaging device 10 is an infrared TV camera that detects a near-infrared light. The imaging device 10 outputs video signals as the result of detection of the near-infrared light.

A touch panel monitor 11 displays a 2-dimensional image of the surface of the fundus oculi Ef (a fundus oculi image Ef') based on the video signals. The video signals are sent to the arithmetic and control unit 200, and the fundus oculi image is displayed on a display (described later).

For imaging the fundus oculi by the imaging device 10, for example, an illumination light having a wavelength of near-infrared region outputted from the imaging light source 103 of the illumination optical system 100 is used.

On the other hand, the image pick-up element 12a is an image pick-up element such as a CCD or a CMOS installed in the imaging device 12 such as a TV camera, and particularly detects a light having a wavelength of visible region. That is to say, the imaging device 12 is a TV camera that detects a visible light. The imaging device 12 outputs video signals as the result of detection of the visible light.

The touch panel monitor 11 displays a 2-dimensional image of the surface of the fundus oculi Ef (the fundus oculi image Ef') based on the video signals. The video signals are sent to the arithmetic and control unit 200, and the fundus oculi image is displayed on the display (described later).

For imaging the fundus oculi by the imaging device 12, for example, an illumination light having a wavelength of visible region outputted from the observation light source 101 of the illumination optical system 100 is used.

The retinal camera unit 1A is provided with a scan unit 141 and a lens 142. The scan unit 141 includes a configuration for scanning an application position of the light outputted from the OCT unit 150 (the signal light LS; described later) on the fundus oculi Ef.

The lens 142 collimates the signal light LS guided from the OCT unit 150 through the connection line 152 and makes the light enter the scan unit 141. Further, the lens 142 focuses the fundus oculi reflection light of the signal light LS propagated through the scan unit 141.

FIG. 2 shows an example of the configuration of the scan unit 141. The scan unit 141 includes Galvano mirrors 141A and 141B, and reflection mirrors 141C and 141D.

The Galvano mirrors 141A and 141B are reflection mirrors disposed so as to be rotatable about rotary shafts 141a and 141b, respectively. The Galvano mirrors 141A and 141B are rotated about the rotary shafts 141a and 141b, respectively, by drive mechanisms described later (mirror drive mechanisms 241 and 242 shown in FIG. 5). Consequently, the reflection faces (the faces reflecting the signal light LS) of the Galvano mirrors 141A and 141B are turned around.

The rotary shafts 141a and 141b are arranged orthogonally to each other. In FIG. 2, the rotary shaft 141a of the Galvano mirror 141A is arranged in parallel to the paper face. On the other hand, the rotary shaft 141b of the Galvano mirror 141B is arranged in the orthogonal direction to the paper face.

That is to say, the Galvano mirror 141B is formed so as to be rotatable in the directions indicated by an arrow pointing in both directions in FIG. 2, whereas the Galvano mirror 141A is formed so as to be rotatable in the directions orthogonal to the arrow pointing in both the directions. Consequently, the Galvano mirrors 141A and 141B act so as to change directions to reflect the signal light LS into directions orthogonal to each other. As seen from FIGS. 1 and 2, a scan with the signal light LS is performed in the x-direction when the Galvano mirror 141A is rotated, and a scan with the signal light LS is performed in the y-direction when the Galvano mirror 141B is rotated.

The signal light LS reflected by the Galvano mirrors 141A and 141B is reflected by reflection mirrors 141C and 141D, thereby traveling in the same direction as having entered the Galvano mirror 141A.

An end face 152b of the optical fiber 152a inside the connection line 152 is arranged facing the lens 142. The signal light LS emitted from the end face 152b travels expanding its beam diameter toward the lens 142, and is collimated by the lens 142. On the contrary, the signal light LS propagated through the fundus oculi Ef is focused to the end face 152b by the lens 142, and enters the optical fiber 152a.

[Configuration of OCT Unit]

Next, the configuration of the OCT unit 150 will be described with reference to FIG. 3. The OCT unit 150 is a device for forming a tomographic image of the fundus oculi based on optically acquired data (data detected by a CCD 184 described later).

The OCT unit 150, together with the optical members in the retinal camera unit 1A that form the light path of the signal light and an image forming part 220 described later, configures an example of the "image forming part" of the present invention.

The OCT unit 150 has almost the same optical system as a conventional optical image measurement device. That is to say, the OCT unit 150 splits a low-coherence light into a reference light and a signal light and superimposes the signal light propagated through an eye with the reference light propagated through a reference object, thereby generating and detecting an interference light. The result of this detection (a detection signal) is inputted to the arithmetic and control unit 200. The arithmetic and control unit 200 forms a tomographic image of the eye by analyzing the detection signal.

A low-coherence light source 160 is composed of a broadband light source, such as a super luminescent diode (SLD) or a light emitting diode (LED), which outputs a low-coherence light L0. The low-coherence light L0 is, for example, a light including a light having a wavelength of near-infrared region and having a temporal coherence length of approximately several tens of micrometers.

The low-coherence light L0 has a longer wavelength than the illumination light of the retinal camera unit 1A (a wavelength of about 400~800 nm), for example, a wavelength included in a range of about 800~900 nm.

The low-coherence light L0 outputted from the low-coherence light source 160 is guided to an optical coupler 162 through an optical fiber 161. The optical fiber 161 is composed of, for example, a single mode fiber or a PM (Polarization maintaining) fiber. The optical coupler 162 splits the low-coherence light L0 into a reference light LR and the signal light LS.

Although the optical coupler 162 acts as both a part for splitting a light (a splitter) and a part for superimposing lights (coupler), it will be herein referred to as an "optical coupler" idiomatically.

The reference light LR generated by the optical coupler 162 is guided by an optical fiber 163 composed of a single mode fiber or the like, and emitted from the end face of the fiber. Furthermore, the reference light LR is collimated by a collimator lens 171, propagated through a glass block 172 and a density filter 173, and reflected by a reference mirror 174. The reference mirror 174 is an example of the "reference object" of the present invention.

The reference light LR reflected by the reference mirror 174 is again propagated through the density filter 173 and the glass block 172, focused to the fiber end face of the optical fiber 163 by the collimator lens 171, and guided to the optical coupler 162 through the optical fiber 163.

The glass block 172 and the density filter 173 act as a delaying part for matching the light path lengths (optical distances) of the reference light LR and the signal light LS, and also act as a dispersion compensation part for matching the dispersion characteristics of the reference light LR and the signal light LS.

The density filter 173 also acts as a dark filter that reduces the amount of the reference light, and is composed of a rotating ND (neutral density) filter, for example. The density filter 173 acts so as to change the reduction amount of the reference light LR by being rotary driven by a drive mechanism including a driver such as a motor (a density-filter drive mechanism 244 described later; refer to FIG. 5). Consequently, it is possible to change the amount of the reference light LR contributing to generation of an interference light LC.

Further, the reference mirror 174 is configured to move in the traveling direction of the reference light LR (the direction of the arrow pointing both sides shown in FIG. 3). Consequently, it is possible to ensure the light path length of the reference light LR corresponding to the axial length of the eye E, the working distance (the distance between the objective lens 113 and the eye E), and the like. Moreover, it is possible to acquire an image at any depth position of the fundus oculi Ef, by moving the reference mirror 174. The reference mirror 174 is moved by a drive mechanism (a reference-mirror drive mechanism 243 described later; refer to FIG. 5) including a driver such as a motor.

On the other hand, the signal light LS generated by the optical coupler 162 is guided to the end of the connection line 152 through an optical fiber 164 composed of a single mode fiber or the like. The conductive optical fiber 152a runs inside the connection line 152. The optical fiber 164 and the optical fiber 152a may be composed of one optical fiber, or may be integrally formed by connecting the end faces of the respective fibers. In either case, it is sufficient as far as the optical fiber 164 and 152a are configured to be capable of transferring the signal light LS between the retinal camera unit 1A and the OCT unit 150.

The signal light LS is guided through the inside of the connection line 152 and led to the retinal camera unit 1A. Furthermore, the signal light LS is propagated through the lens 142, the scan unit 141, the dichroic mirror 134, the imaging lens 126, the relay lens 125, the variable magnifying lens 124, the imaging diaphragm 121, the aperture 112a of the aperture mirror 112 and the objective lens 113, and is projected to the eye E. The barrier filters 122 and 123 are retracted from the light path in advance, respectively, when the signal light LS is projected to the eye E.

The signal light LS having entered the eye E forms an image on the fundus oculi Ef, and thereafter, is reflected. In this case, the signal light LS is not only reflected on the surface of the fundus oculi Ef but also scattered at the refractive index boundary after reaching the deep area of the fundus oculi Ef. Therefore, the signal light LS propagated through the fundus oculi Ef contains information reflecting the surface morphology of the fundus oculi Ef and information reflecting the state of backscatter at the refractive index boundary of the deep area tissue of the fundus oculi Ef. This light may be simply referred to as the "fundus oculi reflection light of the signal light LS."

The fundus oculi reflection light of the signal light LS reversely travels along the abovementioned path within the retinal camera unit 1A, and is focused to the end face 152b of the optical fiber 152*a*. Then, the signal light LS enters the OCT unit 150 through the optical fiber 152*a*, and returns to the optical coupler 162 through the optical fiber 164.

The optical coupler 162 superimposes the signal light LS returned through the eye E and the reference light LR reflected by the reference mirror 174 to generate the interference light LC. The generated interference light LC is guided into a spectrometer 180 through an optical fiber 165 composed of a single mode fiber or the like.

Although a Michelson-type interferometer is adopted in this embodiment, it is possible to appropriately employ an interferometer of any type such as Mach Zender type.

The spectrometer 180 includes a collimator lens 181, a diffraction grating 182, an image forming lens 183, and a CCD 184. The diffraction grating 182 may be a transmission-type diffraction grating that transmits light, or may be a reflection-type diffraction grating that reflects light. Moreover, it is also possible to use, instead of the CCD 184, another photodetecting element such as a CMOS.

The interference light LC having entered the spectrometer 180 is collimated by the collimator lens 181 and divided into spectra (spectral resolution) by the diffraction grating 182. The interference light LC divided into spectra is formed into an image on the image pick-up face of the CCD 184 by the image forming lens 183. The CCD 184 detects the respective spectra of the divided interference light LC and converts into electrical detection signals, and outputs the detected signals to the arithmetic and control unit 200.

[Configuration of Arithmetic and Control Unit]

Next, the configuration of the arithmetic and control unit 200 will be described. The arithmetic and control unit 200 analyzes the detection signals inputted from the CCD 184 of the OCT unit 150, and forms a tomographic image of the fundus oculi Ef. This analysis method is the same as the conventional Fourier Domain OCT method.

Further, the arithmetic and control unit 200 forms a 2-dimensional image showing the surface morphology of the fundus oculi Ef, based on the video signals outputted from the imaging devices 10 and 12 of the retinal camera unit 1A.

Furthermore, the arithmetic and control unit 200 controls each part of the retinal camera unit 1A and the OCT unit 150.

As control of the retinal camera unit 1A, the arithmetic and control unit 200 executes, for example: control of output of the illumination light by the observation light source 101 and the imaging light source 103; control of insertion/retraction operations of the exciter filters 105 and 106 or the barrier filters 122 and 123 to/from the light path; control of the operation of a display device such as the LCD 140; control of movement of the illumination diaphragm 110 (control of the diaphragm value); control of the diaphragm value of the imaging diaphragm 121; and control of movement of the variable magnifying lens 124 (control of the magnification). Moreover, the arithmetic and control unit 200 executes control of the operations of the Galvano mirrors 141A and 141B.

As control of the OCT unit 150, the arithmetic and control unit 200 executes, for example: control of output of the low-coherence light L0 by the low-coherence light source 160; control of movement of the reference mirror 174; control of the rotary operation of the density filter 173 (the operation of changing the reduction amount of the reference light LR); and control of the accumulation time of the CCD 184.

The hardware configuration of the arithmetic and control unit 200 will be described with reference to FIG. 4.

The arithmetic and control unit 200 is provided with a similar hardware configuration to that of a conventional computer. To be specific, the arithmetic and control unit 200 includes a microprocessor 201, a RAM 202, a ROM 203, a hard disk drive (HDD) 204, a keyboard 205, a mouse 206, a display 207, an image forming board 208, and a communication interface (I/F) 209. These parts are connected via a bus 200*a*.

The microprocessor 201 includes a CPU (Central Processing Unit), an MPU (Micro Processing Unit) or the like. The microprocessor 201 executes operations characteristic to this embodiment, by loading a control program 204*a* stored in the hard disk drive 204, onto the RAM 202.

Further, the microprocessor 201 executes control of each part of the device described above, various arithmetic processes, and so on. Further, the microprocessor 201 receives an operation signal from the keyboard 205 or the mouse 206, and executes control of each part of the device in response to the operation content. Furthermore, the microprocessor 201 executes control of a display process by the display 207, control of a transmission/reception process of data and signals by the communication interface 209.

The keyboard 205, the mouse 206 and the display 207 are used as user interfaces in the fundus oculi observation device 1. The keyboard 205 is used as, for example, a device for typing letters, figures, and so on. The mouse 206 is used as a device for performing various input operations to the display screen of the display 207.

Further, the display 207 is a display device such as an LCD and a CRT (Cathode Ray Tube) display, and displays various images like an image of the fundus oculi Ef formed by the fundus oculi observation device 1, or displays various screens such as an operation screen and a set-up screen.

The user interface of the fundus oculi observation device 1 is not limited to the above configuration, and may include a track ball, a control lever, a touch panel type of LCD, a control panel for ophthalmic examinations, and so on. As the user interface, it is possible to employ any configuration having a function of displaying and outputting information and a function of inputting information and operating the device.

The image forming board 208 is a dedicated electronic circuit for forming (image data of) an image of the fundus oculi Ef. The image forming board 208 is provided with a fundus oculi image forming board 208*a* and an OCT image forming board 208*b*.

The fundus oculi image forming board 208*a* is a dedicated electronic circuit that forms image data of a fundus oculi image based on the video signals from the imaging device 10 and the imaging device 12.

Further, the OCT image forming board 208*b* is a dedicated electronic circuit that forms image data of a tomographic image of the fundus oculi Ef, based on the detection signals from the CCD 184 of the OCT unit 150.

By disposing the image forming board 208, it is possible to increase the processing speed of a process for a forming fundus oculi image and a tomographic image.

The communication interface 209 sends control signals from the microprocessor 201, to the retinal camera unit 1A or the OCT unit 150. Moreover, the communication interface 209 receives video signals from the imaging devices 10 and 12 or detection signals from the CCD 184 of the OCT unit 150, and inputs the signals to the image forming board 208. In this case, the communication interface 209 operates to input the video signals from the imaging devices 10 and 12, to the fundus oculi image forming board 208*a*, and input the detection signals from the CCD 184, to the OCT image forming board 208*b*.

Further, in a case that the arithmetic and control unit 200 is connected to a communication network such as a LAN (Local Area Network) or the Internet, it is possible to configure to be capable of data communication via the communication network, by providing the communication interface 209 with a network adapter like a LAN card or communication equipment like a modem. In this case, by mounting a server accommodating the control program 204a on the communication network, and also configuring the arithmetic and control unit 200 as a client terminal of the server, it is possible to make the fundus oculi observation device 1 operate.

[Configuration of Control System]

Next, the configuration of the control system of the fundus oculi observation device 1 will be described with reference to FIGS. 5 and 6.

(Controller)

The control system of the fundus oculi observation device 1 is configured mainly having a controller 210 of the arithmetic and control unit 200. The controller 210 includes the microprocessor 201, the RAM 202, the ROM 203, the hard disk drive 204 (the control program 204a), and the communication interface 209.

The controller 210 executes the aforementioned control by the microprocessor 201 that operates based on the control program 204a. The controller 201 is provided with the main controller 211 and the storage 212.

(Main Controller)

The main controller 211 controls the mirror drive mechanisms 241 and 242 to control the positions of the Galvano mirrors 141A and 141B, thereby scanning the application position of the signal light LS on the fundus oculi Ef. Moreover, the main controller 211 controls the LCD 140 to display the internal fixation target. In particular, the main controller 211 simultaneously controls the mirror drive mechanisms 241 and 242 and the LCD 140 to present the internal fixation target on the eye E and scan with the signal light LS. The main controller 211 is an example of the "controller" of the present invention.

The main controller 211 executes, for example, control of the low-coherence light source 160 to turn on/off, control of the CCD 184, control of the density-filter drive mechanism 244 for rotating the density filter 173, and control of the reference-mirror drive mechanism 243 for moving the reference mirror 174 in the traveling direction of the reference light LR.

Further, the main controller 211 controls a display 240A of the user interface (UI) 240 to display two kinds of images captured by the fundus oculi observation device 1, namely, the fundus oculi image Ef' and a tomographic image. These images may be displayed on the display 240A separately, or may be displayed side by side.

(Storage)

The storage 212 stores image data of the fundus oculi image Ef', image data of an OCT image such as a tomographic image of the fundus oculi Ef and a three-dimensional image, and so on. Moreover, the storage 212 stores various types of data, such as data regarding examinations and data regarding patients. A process of writing the data into the storage 212 and a process of reading out the data from the storage 212 are executed by the main controller 211.

(Image Forming Part)

The image forming part 220 forms image data of the fundus oculi image Ef' based on the video signals outputted from the imaging devices 10 and 12. The image forming part 220 also forms image data of the tomographic image of the fundus oculi Ef based on the detection signals outputted from the CCD 184 of the OCT unit 150.

The imaging forming part 220 includes the image forming board 208, the communication interface 209, and so on. In this specification, "image" may be identified with "image data" corresponding thereto.

(Image Processor)

The image processor 230 applies various kinds of image processing and analysis processes to image data of images formed by the image forming part 220. For example, the image processor 230 executes various kinds of correction processes such as luminance correction and dispersion correction of the images.

Further, the image processor 230 executes, on tomographic images formed by the image forming part 220, an interpolation process of interpolating pixels between the tomographic images, and so on, thereby forming image data of a 3-dimensional image of the fundus oculi Ef.

Image data of a 3-dimensional image is image data made by assigning pixel values to each of a plurality of voxels arranged 3-dimensionally. This image data is referred to as volume data, voxel data, or the like. In the case of displaying an image based on volume data, the image processor 230 executes a rendering process (such as volume rendering or MIP (Maximum Intensity Projection)) on this volume data, and forms image data of a pseudo 3-dimensional image seen from a specific view direction. On a display device such as the display 207, the pseudo 3-dimensional image based on the image data is displayed.

Further, the image processor 230 is also capable of forming stack data of a plurality of tomographic images. Stack data is image data that can be obtained by arranging a plurality of tomographic images acquired along a plurality of scanning lines, based on the positional relation of the scanning lines.

The image processor 230 includes a fixation-state determining part 231 and an image position corrector 232.

(Fixation-State Determining Part)

The fixation-state determining part 231 determines whether the fixation state of the eye E is proper based on an image of the fundus oculi Ef. The image of the fundus oculi Ef is, for example, a two-dimensional image of the surface of the fundus oculi Ef and a tomographic image of the fundus oculi. This image may be either a still image or a motion image.

In a case that this image is a motion image, the fixation-state determining part 231 determines whether the fixation state is proper for each of the frames composing the motion image. Here, whether the fixation state is proper may be determined for each of all the frames composing the motion image, or whether the fixation state is proper may be determined only for frames selected from among all the frames. As an example of the litter, there is a method of determining whether the fixation state is proper at every predetermined number of frames.

A specific example of the operation of the fixation-state determining part 231 will now be described. The fixation-state determining part 231 analyzes an image of the fundus oculi Ef to specify the image position of a characteristic site of the fundus oculi Ef within the image and determines whether the fixation state is proper based on this image position. In this case, it is possible to shorten a time required for the process by specifying the image position of the characteristic site based on the luminance distribution in the entire image or in part of the image.

Firstly, a process for specifying an image position of a characteristic site of the fundus oculi will be described. A characteristic site in a two-dimensional image of the fundus oculi surface is, for example, the macula, the optic papilla, and a vascular branching point. The image position of the macula can be specified by, for example, extracting a substantially circular region that is darker (i.e., the luminance is lower) than the surrounding area from the two-dimensional image. The image position of the optic papilla can be specified by, for example, extracting a substantially circular region that is brighter (i.e., the brightness is higher) than the surrounding area from the two-dimensional image. The image position of the optic papilla can also be specified by extracting the brightest substantially circular region in the image. The image position of the vascular branching point can be specified by, for example, extracting an image region corresponding to a vessel from the two-dimensional image, generating a wire model of this extracted region, and obtaining the branching point of this wire model. These processes may be actualized by analyzing the pixel values of the two-dimensional image.

Moreover, a characteristic site in a tomographic image is, for example, the macula, the optic papilla, a layer of the fundus oculi, and a vessel. The image position of the macula can be specified by, for example, extracting a region corresponding to the fundus oculi surface from the tomographic image and determining the position of a hollow in this region. The image position of the optic papilla can be specified by, for example, specifying a region corresponding to the fundus oculi surface from the tomographic image and determining the position of a large hollow in this region. The image position of a layer of the fundus oculi can be specified by, for example, extracting a region corresponding to the layer of interest from the tomographic image. The layer of the fundus oculi is, for example, the retina, the choroidea, and the sclera. Moreover the retina is composed of an internal limiting membrane, an optic nerve fiber layer, a ganglion cell layer, an inner plexiform layer, an inner granular layer, an outer plexiform layer, an outer granular layer, an external limiting membrane, a photoreceptor layer, a retinal pigment epithelium, and so on. The image position of a vessel can be specified as, for example, a region in the tomographic image corresponding to the vessel. In the tomographic image, since there is a case that an image of a portion deeper than the vessel is not clearly depicted, a region corresponding to the vessel can be specified by specifying such an unclear region.

Next, a process for determining whether the fixation state is proper will be described. Firstly, a predetermined position within the frame of an image of the fundus oculi Ef is set as a reference position. As a reference position, for example, the center position of the frame can be used. The fixation-state determining part 231 obtains a displacement of the image position of the characteristic site with respect to the reference position. This displacement can be calculated with, for example, the Pythagorean theorem based on the coordinate values of the reference position and the coordinate values of the image position of the characteristic site. Moreover, the displacement may be obtained as a displacement component in each coordinate direction. Moreover, the displacement may be obtained as the number of pixels from the reference position to the image position of the characteristic site.

The fixation-state determining part 231 compares (the size of) the displacement with a predetermined threshold. This threshold is preset. When the displacement is equal to or less than the threshold, the fixation-state determining part 231 determines that the fixation state is proper, namely, fixation has been properly done at the time of acquisition of the image. On the other hand, when the displacement exceeds the threshold, the fixation-state determining part 231 determines that the fixation state is improper, namely, fixation has not been properly done at the time of acquisition of the image. The factor causing the improper fixation state is, for example, the eye E having followed the trajectory of the scan with the signal light LS.

Another example of the determining process will be described. Firstly, a predetermined region within the frame of an image is set as a reference region. The reference region is set as, for example, a predetermined size of region in the center of the frame. This size can be set to, for example, about the above threshold.

The fixation-state determining part 231 determines whether the image position of the characteristic site is included within the reference region. It is possible to execute this process by comparing the pixel positions of the both. When it is determined that the image position of the characteristic site is included in the reference position, the fixation-state determining part 231 determines the fixation state is proper. On the other hand, when it is determined that the image position is not included, the fixation-state determining part 231 determines the fixation state is improper.

The fixation-state determining part 231 that operates as described above, together with the aforementioned imaging part and the image forming part, configures an example of the "determining part" of the present invention.

(Image Position Corrector)

The image position corrector 232 operates when the fixation-state determining part 231 has calculated the aforementioned displacement based on the two-dimensional image of the fundus oculi surface. The image position corrector 232 corrects the position of the tomographic image of the fundus oculi Ef based on this displacement. This process is executed by changing the position of the tomographic image in the xy-directions (the position on the fundus oculi surface) so as to cancel the displacement. For example, in a case that the displacement is (Δx, Δy), the image position corrector 232 changes the x-coordinate value of the tomographic image by −Δx and changes the y-coordinate value by −Δy.

The image processor 230 operating as described above includes the microprocessor 201, the RAM 202, the ROM 203, the hard disk drive 204 (the control program 204a), and so on.

The image position corrector 232 that operates as described above is an example of the "corrector" of the present invention.

(User Interface)

The user interface (UI) 240 is provided with the display 240A and the manipulation part 240B. The display 240A is composed of a display device such as a display 207. The manipulation part 240B is composed of an input device and manipulation device such as a keyboard 205 and a mouse 206.

[Scan with Signal Light and Image Processing]

A scan with the signal light LS is performed by turning around the reflecting surfaces of the Galvano mirrors 141A and 141B of the scan unit 141 as described before. The controller 210 controls the mirror drive mechanisms 241 and 242, respectively, to turn around the reflecting surfaces of the Galvano mirrors 141A and 141B, respectively, thereby scanning the fundus oculi Ef with the signal light LS.

When the reflecting surface of the Galvano mirror 141A is turned around, a scan with the signal light LS in the horizontal direction (the x-direction in FIG. 1) is performed on the fundus oculi Ef. On the other hand, when the reflecting surface of the Galvano mirror 141B is turned around, a scan with the signal light LS in the vertical direction (the y-direction in FIG. 1) is performed on the fundus oculi Ef. Further, by turning around both the reflecting surfaces of the Galvano mirrors 141A and 141B simultaneously, it is possible to scan with the signal light LS in the composed direction of the x-direction and y-direction. That is to say, by controlling the two Galvano mirrors 141A and 141B, it is possible to scan with the signal light LS in any direction on the x-y plane.

Figure 7A:
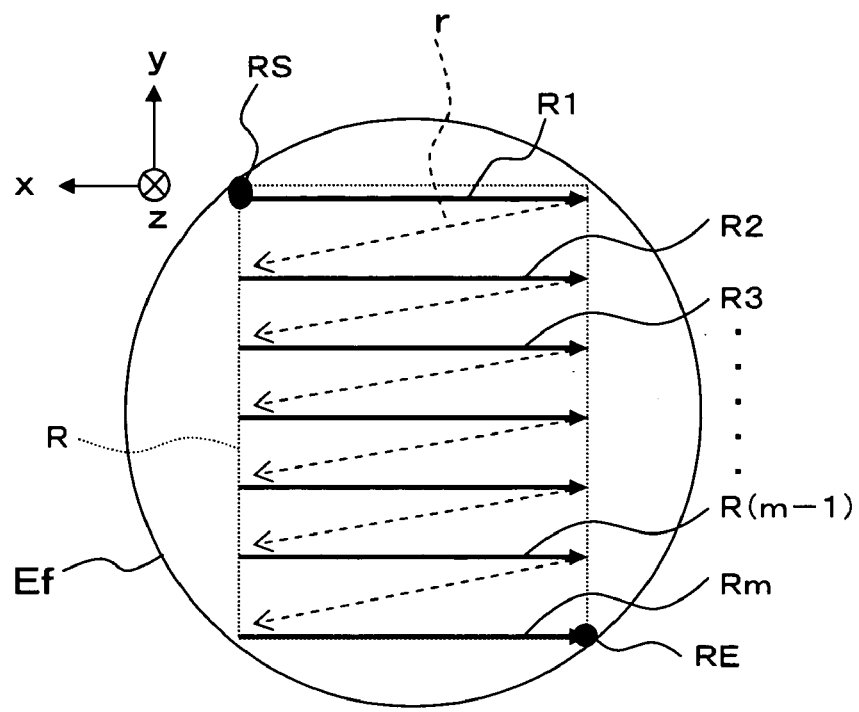
FIGS. 7A and 7B are schematic views showing an example of a scanning pattern of a signal light in the embodiment of the fundus oculi observation device functioning as the optical image measurement device according to the present invention.
Figure 7B:
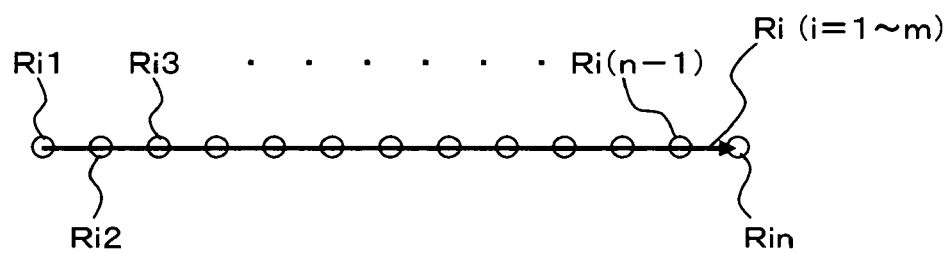

FIGS. 7A and 7B show an example of a scanning pattern of the signal light LS for forming an image of the fundus oculi Ef. FIG. 7A shows an example of the scanning pattern of the signal light LS when the fundus oculi Ef is seen from a direction in which the signal light LS enters the eye E (namely, seen from the −z-side to the +z-side in FIG. 1). FIG. 7B shows an example of an arrangement pattern of scanning points (positions to perform image measurement) on each scanning line on the fundus oculi Ef.

As shown in FIG. 7A, a scan with the signal light LS is performed within a rectangular scanning region R set in advance.

Within the scanning region R, a plurality of (m lines of) scanning lines R1~Rm are set in the x-direction. When a scan with the signal light LS is performed along each scanning line Ri (i=1~m), a detection signal of the interference light LC is generated.

A direction of each scanning line Ri will be referred to as the "main scanning direction," and a direction orthogonal thereto will be referred to as the "sub-scanning direction." Accordingly, a scan with the signal light LS in the main scanning direction is performed by turning around the reflecting surface of the Galvano mirror 141A. A scan in the sub-scanning direction is performed by turning around the reflecting surface of the Galvano mirror 141B.

On each scanning line Ri, as shown in FIG. 7B, a plurality of (n pieces of) scanning points Ri1~Rin are preset.

In order to execute the scan shown in FIGS. 7A and 7B, the controller 210 firstly controls the Galvano mirrors 141A and 141B to set the entering target of the signal light LS on the fundus oculi Ef to a scan start position RS (a scanning point R11) on the first scanning line R1. Subsequently, the controller 210 controls the low-coherence light source 160 to flush the low-coherence light L0, thereby making the signal light LS enter the scan start position RS. The CCD 184 receives the interference light LC based on the fundus oculi reflection light of the signal light LS at the scan start position RS, and outputs the detection signal to the controller 210.

Next, the controller 210 controls the Galvano mirror 141A to scan with the signal light LS in the main scanning direction and set the entering target to a scanning point R12, and controls to flush the low-coherence light L0 and make the signal light LS enter a scanning point R12. The CCD 184 receives the interference light LC based on the fundus oculi reflection light of the signal light LS at the scanning point R12, and outputs the detection signal to the controller 210.

In the same way, the controller 210 controls to flush the low-coherence light L0 at each scanning point while sequentially moving the entering target of the signal light LS in order of a scanning point R13, R14, ---, R1(n−1) and R1n, thereby acquiring a detection signal outputted from the CCD 184 in response to the interference light LC for each scanning point.

When the measurement at the last scanning point R1n of the first scanning line R1 ends, the controller 210 controls the Galvano mirrors 141A and 141B simultaneously to move the entering target of the signal light LS to a first scanning point R21 of a second scanning line R2 along a line switching scan r. Then, by executing the aforementioned measurement for each scanning point R2j (j=1~n) of the second scanning line R2, a detection signal corresponding to each scanning point R2j is acquired.

In the same way, the measurement is performed for each of a third scanning line R3, ---, an m−1th scanning line R(m−1) and an mth scanning line Rm, whereby a detection signal corresponding to each scanning point is acquired. Symbol RE on the scanning line Rm is a scan end position corresponding to a scanning point Rmn.

Consequently, the controller 210 acquires m×n pieces of detection signals corresponding to m×n pieces of scanning points Rij (i=1~m, j=1~n) within the scanning region R. Hereinafter, a detection signal corresponding to the scanning point Rij may be represented by Dij.

Interlocking control of the movement of the scanning point and the output of the low-coherence light L0 as described above can be implemented by synchronizing a transmission timing of a control signal to the mirror drive mechanisms 241 and 242 and a transmission timing of a control signal to the low-coherence light source 160.

When controlling to make the respective Galvano mirrors 141A and 141B operate as described above, the controller 210 stores the position of the scanning line Ri and the position of the scanning point Rij (coordinates on the x-y coordinate system) as information representing the content of the operation. This stored content (the scan position information) is used in an image forming process and so on as conventional.

Next, an example of image processing in the case of a scan with the signal light LS shown in FIGS. 7A and 7B will be described.

The image forming part 220 forms tomographic images of the fundus oculi Ef along each scanning line Ri (the main scanning direction). Further, the image processor 230 forms a 3-dimensional image of the fundus oculi Ef based on the tomographic images formed by the image forming part 220.

A process of forming tomographic images by the image forming part 220 includes a two-step arithmetic process as conventional. In the first step of the arithmetic process, based on the detection signal Dij corresponding to each scanning point Rij, an image in the depth direction (the z-direction in FIG. 1) of the fundus oculi Ef at the scanning point Rij is formed.

Figure 8:
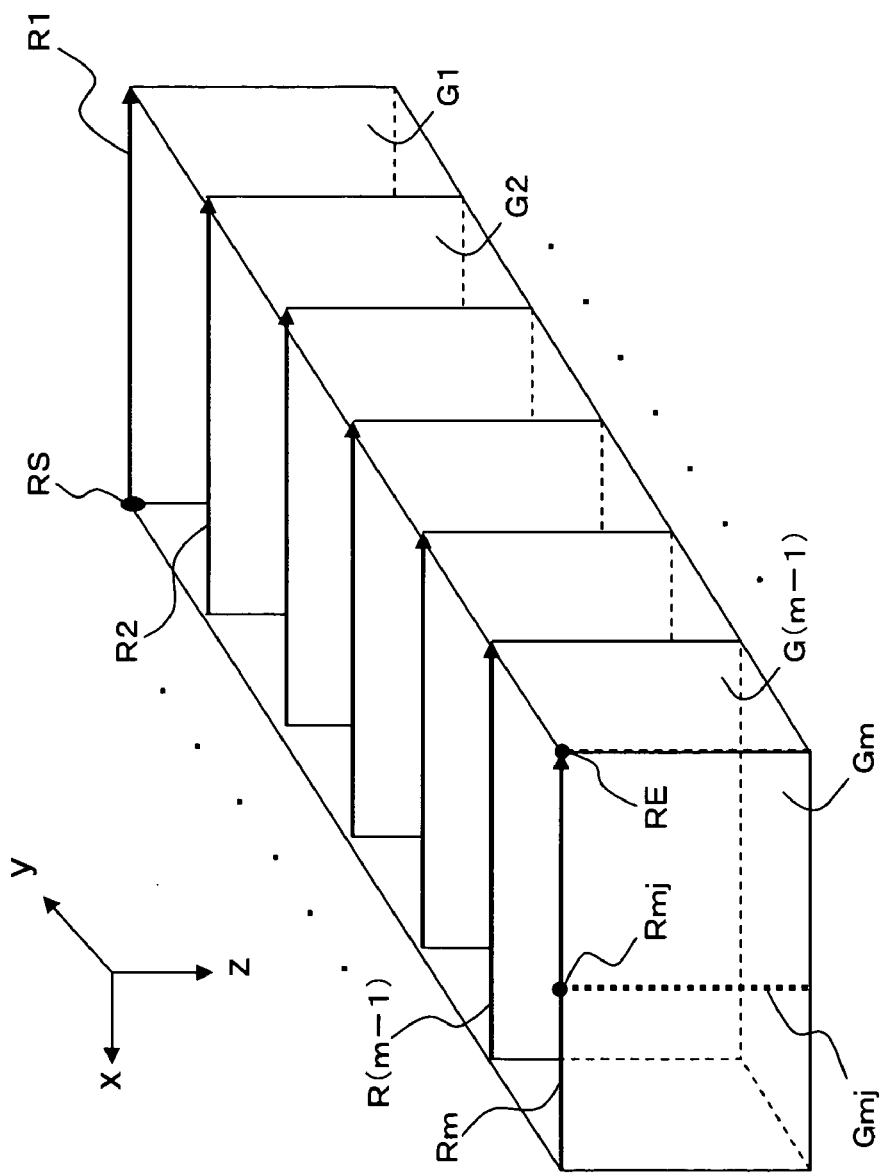
FIG. 8 is a schematic view showing an example of the scanning pattern of the signal light and a pattern of a tomographic image formed along each scanning line in the embodiment of the fundus oculi observation device functioning as the optical image measurement device according to the present invention.

FIG. 8 shows a pattern of tomographic images formed by the image forming part 220. In the second step of the arithmetic process, for each scanning line Ri, based on the depthwise images at the n pieces of scanning points Ri1~Rin, a tomographic image Gi of the fundus oculi Ef along the scanning line Ri is formed. At this moment, the image forming part 220 determines the arrangement and interval of the scanning points Ri1~Rin by referring to the positional information (scan position information described before) of the scanning points Ri1~Rin, and forms the scanning lines Ri. Through this process, it is possible to obtain m pieces of tomographic images G1~Gm at different positions in the sub-scanning direction (y-direction).

Next, a process of forming a 3-dimensional image of the fundus oculi Ef by the image processor 230 will be described. A 3-dimensional image of the fundus oculi Ef is formed based on the m pieces of tomographic images obtained through the abovementioned arithmetic process. The image processor 230 forms a 3-dimensional image of the fundus oculi Ef by, for example, performing a known interpolation process of interpolating an image between the adjacent tomographic images Gi and G(i+1).

In this case, the image processor 230 determines the arrangement and interval of the scanning lines Ri by referring to the positional information of the scanning lines Ri, thereby forming a 3-dimensional image. For this 3-dimensional image, 3-dimensional coordinates (x, y, z) are set, based on the positional information of each scanning point Rij (the aforementioned scan position information) and the z-coordinate of a depthwise image.

Further, based on this 3-dimensional image, the image processor 230 can form a tomographic image of the fundus oculi Ef at a cross section in any direction other than the main scanning direction (x-direction). When the cross section is designated, the image processor 230 specifies the positions of the respective scanning points (and/or interpolated depthwise images) on this designated cross section, extracts depthwise images at the respective specified positions (and/or interpolated depthwise images) from the 3-dimensional image, and arranges the plurality of extracted depthwise images, thereby forming a tomographic image of the fundus oculi Ef at the designated cross section.

An image Gmj shown in FIG. 8 represents a depthwise (z-direction) image at the scanning point Rmj on the scanning line Rm. In the same way, a depthwise image at each scanning point Rij on each scanning line Ri formed in the aforementioned first-step of arithmetic process will be referred to as the "image Gij."

[Usage Patterns]

Usage patterns of the fundus oculi observation device 1 will now be described. In these usage patterns, a usage pattern in which practice for fixation is conducted before acquisition of an OCT image, and a usage pattern in which it is determined whether the fixation state is proper will be described.

[First Usage Pattern]

Figure 9:
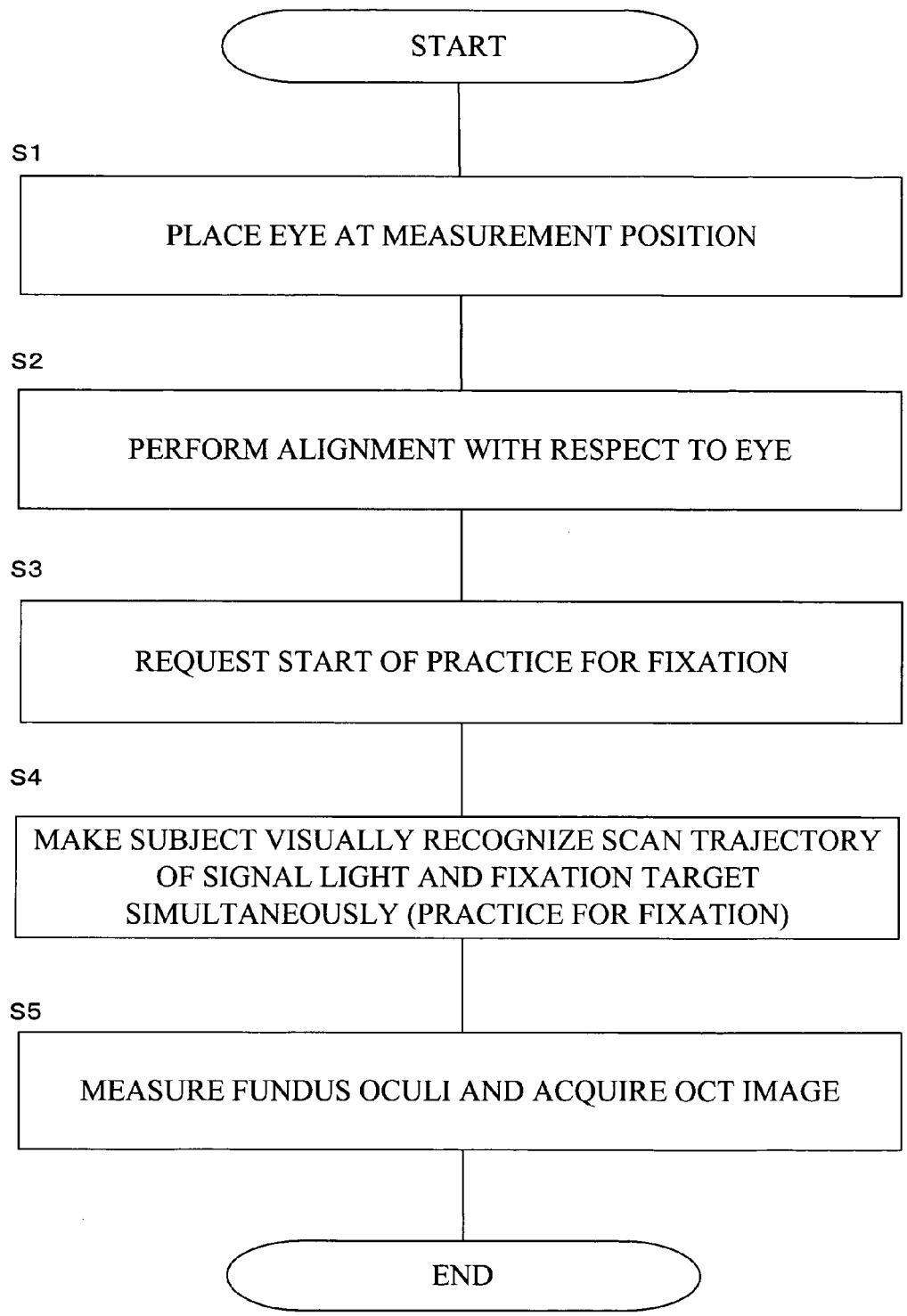
FIG. 9 is a flow chart showing an example of a usage pattern of the embodiment of the fundus oculi observation device functioning as the optical image measurement device according to the present invention.

The usage pattern in which practice for fixation is conducted before acquisition of an OCT image will be described. A flow chart shown in FIG. 9 represents an example of this usage pattern.

Firstly, the eye E is placed at a predetermined measurement position (a position facing the objective lens 113) (S1). Like a conventional retinal camera, the fundus oculi observation device 1 is provided with a jaw holder and a forehead protector that are used for fixing the position of the eye E (not shown).

Next, alignment of the optical system of the device with respect to the eye E is performed (S2). As in a conventional retinal camera, the alignment is executed by using an alignment bright point or a scale. When the alignment is completed, the operator operates the manipulation part 240B to request start of the practice for fixation (S3).

The main controller 211 having received this request controls the low-coherence light source 160 and the mirror drive mechanisms 241 and 242 to scan the eye E with the signal light LS and make the subject visually recognize the trajectory of the scan, and also controls the LCD 140 to display a fixation target and make the subject visually recognize the fixation target. Consequently, the subject visually recognizes both the trajectory of the scan with the signal light LS and the fixation target simultaneously (S4).

For example, in the case of executing the scan shown in FIG. 7A, the subject visually recognizes the fixation target and a red line (a line extending in the x-direction) that moves in the vertical direction (y-direction) as the trajectory of the scan. The operator (examiner) advises the subject to stare at the fixation target. It is desirable that such practice for staring at the fixation target is conducted until staring at the fixation target can be steadily obtained in a situation that the trajectory of scan moves.

When the practice is finished, the fundus oculi Ef is measured and an OCT image is acquired (S5). In a case that the eye E is not properly fixed at the time of measurement, it is possible to practice the fixation again. This ends the description of this usage pattern.

[Second Usage Pattern]

Figure 10:
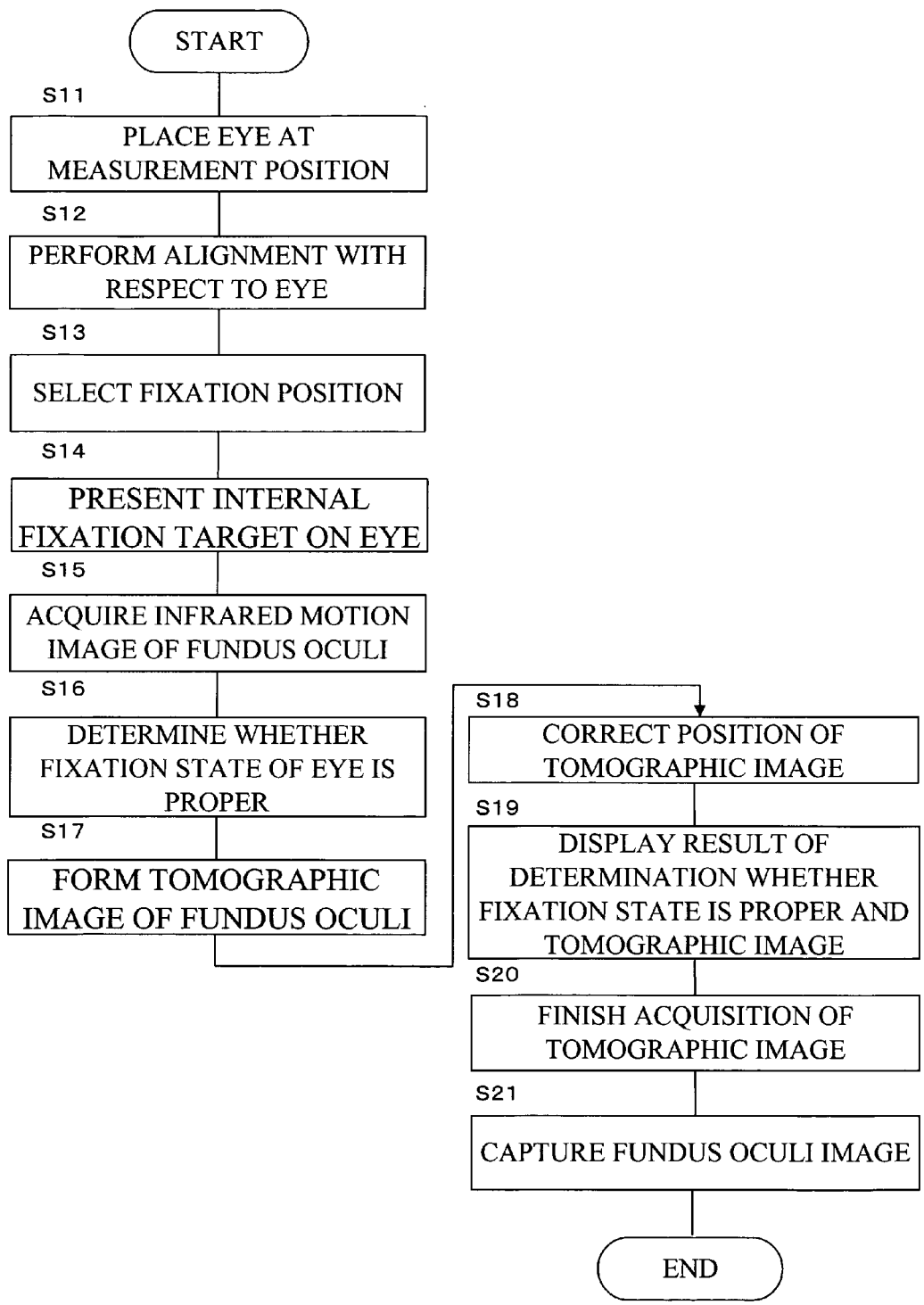
FIG. 10 is a flow chart showing an example of a usage pattern of the embodiment of the fundus oculi observation device functioning as the optical image measurement device according to the present invention.

The usage pattern in which it is determined whether the fixation position is proper will be described. A flow chart shown in FIG. 10 represents an example of this usage pattern.

Firstly, as in the first usage pattern, the eye E is placed at a predetermined measurement position (S11) and alignment is performed (S12).

When the alignment is completed, the operator operates the manipulation part 240B to select a fixation position of the fundus oculi Ef (S13). As mentioned above, the fixation position is, for example, a fixation position for the center of the fundus oculi, a fixation position for the macula, and a fixation position for the optic papilla. The main controller 211 controls the LCD 140 to present an internal fixation target corresponding to the selected fixation position on the eye E (S14).

Furthermore, the main controller 211 controls the imaging light source 103 and the imaging device 10 to acquire an infrared motion image of the fundus oculi Ef (S15). The main controller 211 controls the display 240A to display the infrared motion image in real time.

Moreover, the main controller 211 inputs the frame of the infrared motion image into the image processor 230 in real time. The fixation-state determining part 231 specifies a characteristic site (the macula, optic papilla, or the like) corresponding to the fixation position selected in Step 13, specifies an image position of the characteristic site from the frame of the infrared motion image, and determines whether the fixation state of the eye E is proper (S16). In this usage pattern, the fixation-state determining part 231 obtains the displacement between the reference position and the image position of the characteristic site.

Moreover, for example, in response to an operator's request, the main controller 211 controls the low-coherence light source 160 and the mirror drive mechanisms 241 and 242 to scan with the signal light LS. The image forming part 220 forms a tomographic image of the fundus oculi Ef based on the detection signal from the CCD 184 (S17).

For each tomographic image, the image position corrector 232 corrects the position in the xy-directions of the tomographic image based on the displacement calculated based on the frame of the infrared motion image when the tomographic image has been acquired (S18). The tomographic image with the position corrected is stored into the storage 212 by the main controller 211.

The main controller 211 controls to display the result of determination whether the fixation state is proper and the tomographic image of the fundus oculi Ef with the position corrected on the display 240A, together with the infrared motion image (S19).

As the display pattern of the determination result, for example, it is possible to display a message or image that shows the determination result. The determination result may be displayed only when the fixation state is proper, or may be displayed only when the fixation state is improper.

The display 240A that displays the determination result is an example of the "output part" of the present invention. Information outputted from the output part is not limited to such visual information, and may be auditory information or the like.

When acquisition of the tomographic image is finished (S20), in response to the operator's request, the main controller 211 controls the observation light source 101 and the imaging device 12 to capture the fundus oculi image Ef' (S21). The fundus oculi image Ef' is stored into the storage 212 by the main controller 211. This ends the description of this usage pattern.

[Action and Effect]

The action and effect of the fundus oculi observation device 1 as described above will now be described.

The fundus oculi observation device 1 is an optical image measurement device that splits the low-coherence light L0 into the signal light LS and the reference light LR, superimposes the signal light LS propagated through the eye E and the reference light LR propagated through the reference mirror 174 to generate the interference light LC, detects the interference light LC, and forms a tomographic image of the fundus oculi Ef based on the detection result.

Furthermore, the fundus oculi observation device 1 is provided with the scan unit 141 that scans the fundus oculi Ef with the signal light LS, and the LCD 140 and an optical system that present a fixation target for fixing the eye E. The main controller 211 controls the scan unit 141 to scan the eye E with the signal light LS and also controls the LCD 140 to present the fixation target on the eye E.

According to the fundus oculi observation device 1, it is possible to realize a visual recognition state in acquisition of an OCT image, namely, a state of visually recognizing the trajectory of a scan with the signal light LS and the fixation target, and have the subject practice the fixation. Consequently, it is possible to prevent the eye E from following the trajectory of the scan with the signal light LS in acquisition of an OCT image.

Further, according to the fundus oculi observation device 1, it is possible to acquire an image of the eye E on which a fixation target is presented and to determine whether the fixation state of the eye E is proper based on the image, so that it is possible to properly fix the eye E. Consequently, it is possible to prevent the eye E from following the trajectory of a scan.

In particular, the examiner can easily grasp whether the fixation is proper during practice of the fixation, and therefore, can give an appropriate advice to the subject. Consequently, it is possible to practice the fixation effectively and efficiently.

Moreover, it is possible to easily grasp whether the fixation is proper at the time of acquisition of an OCT image and, when the eye E follows the trajectory of a scan, it is possible to discontinue the measurement to execute re-measurement or practice again. Consequently, it is possible to increase the efficiency of the examination and acquire a highly accurate OCT image.

Further, according to the fundus oculi observation device 1, since it is possible to acquire a motion image of the fundus oculi Ef and determine whether the fixation state is proper in real time for each frame of this motion image, it is possible to acquire an OCT image while determining in real time whether the fixation is proper. Consequently, it is possible to easily acquire a highly accurate OCT image and increase the efficiency of the examination.

[Modification]

The configuration described above is merely an example for favorably implementing the optical image measurement device according to the present invention. Therefore, it is possible to appropriately apply any modification within the scope of the present invention.

In the aforementioned embodiment, the image position of the characteristic site in the acquired image is automatically specified, but the operator may manually designate the image position. For example, in the case of acquiring a motion image, it is possible to designate the image position of the characteristic site in one frame (a reference frame) and, in other frames, specify the image position of the characteristic site by, for example, calculating the image correlation with the designated position in the reference frame. The designation of the image position of the characteristic site can be performed by, for example, a mouse dragging operation.

Further, in the aforementioned embodiment, the fixation position is designated and it is determined whether the fixation state is proper depending on the fixation position, but it is possible to configure so as to designate an observation target site, select a fixation position corresponding thereto, and determine whether a fixation state is proper depending on the fixation position. For example, when the macula is designated as the observation target site, it is possible to determine whether the fixation state is proper, after a fixation position for the macula is automatically selected. The designation of the observation target site may be manually performed by the operator, or may be automatically performed in the case of a follow-up.

Further, in the aforementioned embodiment, the position of a tomographic image is corrected regardless of the result of determination of the fixation state, but it is possible to configure so that the position of the tomographic image is corrected at least when the fixation state is determined improper.

Further, in the aforementioned embodiment, the position of a tomographic image is corrected based on the result of determination of the fixation state, it is possible to correct the position of the tomographic image to be acquired by controlling the Galvano mirrors 141A and 141B based on the result of determination of the fixation state and correct the position of the scanning line Ri.

In the aforementioned embodiment, it is possible to configure so as to discontinue the subsequent processes when the fixation state of the eye is determined to be improper. In particular, in a case that a process that requires time, such as a process of forming a three-dimensional image based on a plurality of tomographic images, is scheduled, it is desirable to discontinue the relevant process. According to this modification, since a wasteful process based on the measurement result obtained in an improper fixation state can be omitted, it is advantageous in that the time and the resource of the microprocessor may be used efficiently.

When practicing the fixation in the aforementioned embodiment, it is possible to scan the eye with the signal light. It is possible to make this signal light interfere with a reference light to generate and detect an interference light and form an image of the eye based on the detection result. In other words, it is possible to configure so as to acquire an image of the eye during the practice for the fixation. Furthermore, it is possible to determine whether the fixation state of the eye during the practice of the fixation is proper and, if proper, it is possible to adopt the image acquired during the practice as the result of the examination. Consequently, the need for re-measurement after the practice is eliminated, and it is possible to shorten the examination time and reduce the burden on the subject.

The fundus oculi observation device of the aforementioned embodiment may have an automatic alignment function. The automatic alignment function is a function of automatically matching the positions between the device optical system and the eye. The automatic alignment function has already been put into practice in conventional ophthalmic devices (an optical image measurement device, a retinal camera, or the like) (for example, refer to Japanese Unexamined Patent Application. Publication No. 2007-175352, and so on). When the fundus oculi observation device is provided with the automatic alignment function, it is possible to use the determining process of a fixation state according to the present invention for determination of whether automatic alignment has been properly performed. This function is thought to be particularly effective when an image of an eye is measured with no examiner, such as when examinations are conducted for many subjects such as in a medical checkup.

In the aforementioned embodiment, by changing the position of the reference mirror 174, a difference in light path length between the light path of the signal light LS and the light path of the reference light LR is changed. However, the method for changing the difference in light path is not limited to the above method. For example, by integrally moving the retinal camera unit 1A and the OCT unit 150 with respect the eye E to change the light path length of the signal light LS, it is possible to change the difference in light path length. Alternatively, by moving the depthwise (z-direction) measurement object (z-direction), it is possible to change the difference in light path length.

Although the fundus oculi observation device described in the aforementioned embodiment includes an optical image measurement device of Fourier-domain type, it is possible to apply the present invention to an optical image measurement device of any type, such as the Time Domain type, Full Field type or the Swept Source type.

Further, although a device for acquiring an OCT image of the fundus oculi is described in the aforementioned embodiment, it is possible to apply the configuration of the aforementioned embodiment to a device capable of acquiring an OCT image of another site in an eye, such as the cornea.

The invention claimed is:

1. An optical image measurement device that splits a low-coherence light into a signal light and a reference light, superimposes the signal light propagated through an eye and the reference light propagated through a reference object to generate an interference light, detects the interference light, and forms a tomographic image of the eye based on a detection result, the optical image measurement device comprising:
a scanner configured to scan the eye with the signal light;
a presenting part configured to present a fixation target for fixing the eye;
a controller configured to control the presenting part to present the fixation target in the eye, and control the scanner to scan the eye with the signal light; and
a determining part configured to acquire an image of the eye in which the fixation target is presented and which is scanned with the signal light, and determine whether a fixation state of the eye is proper, based on the image.

2. The optical image measurement device according to claim 1, wherein the determining part is configured to analyze the image to specify an image position of a characteristic site of the eye within the image, and determine whether the fixation state is proper, based on the image position.

3. The optical image measurement device according to claim 2, wherein the determining part is configured to obtain a displacement of the image position with respect to a predetermined position in a frame of the image, and determine whether the fixation state is proper, based on the displacement.

4. The optical image measurement device according to claim 3, wherein the determining part is configured to determine the fixation state is proper when a size of the displacement is equal to or less than a predetermined threshold, and to determine the fixation state is improper when the size of the displacement is more than the predetermined threshold.

5. The optical image measurement device according to claim 3, further comprising a corrector configured to correct a position of the tomographic image based on the displacement at least when it is determined that the fixation state is improper.

6. The optical image measurement device according to claim 2, wherein the determining part is configured to determine whether the image position is included in a predetermined region within a frame of the acquired image, and to determine the fixation state is proper when it is determined that the image position is included and determine the fixation state is improper when it is determined that the image position is not included.

7. The optical image measurement device according to claim 1, wherein the determining part includes an imaging part configured to capture an image of a fundus oculi surface of the eye to acquire a two-dimensional image as the image, and is configured to determine whether the fixation state is proper, based on the two-dimensional image.

8. The optical image measurement device according to claim 1, wherein the determining part includes an image forming part configured to form the tomographic image as the image, and is configured to determine whether the fixation state is proper, based on the tomographic image.

9. The optical image measurement device according to claim 1, wherein the determining part is configured to acquire a motion image of a fundus oculi of the eye, and is configured to determine whether the fixation state is proper for each frame of the motion image.

10. The optical image measurement device according to claim 1, further comprising an output part configured to output a determination result of the fixation state by the determining part.

11. The optical image measurement device according to claim 1, wherein:
the presenting part is configured to be capable of selectively presenting a plurality of fixation targets of different fixation positions; and
the determining part is configured to determine whether the fixation state is proper in response to a fixation position of a presented fixation target.

12. An optical image measurement device that splits a low-coherence light into a signal light and a reference light, superimposes the signal light propagated through an eye and the reference light propagated through a reference object to generate an interference light, detects the interference light, and forms a tomographic image of the eye based on a detection result, the optical image measurement device comprising:
a scanner configured to scan the eye with the signal light;
a presenting part configured to present a fixation target for fixing the eye; and
a controller configured to, before detection of the interference light for forming the tomographic image of the eye, control the presenting part to present the fixation target in the eye, and control the scanner to scan the eye with the signal light.

* * * * *